(12) United States Patent
Bley et al.

(10) Patent No.: US 9,663,413 B2
(45) Date of Patent: May 30, 2017

(54) PRIMER COMPOSITION

(75) Inventors: Ulrich Bley, Fürth (DE); Rainer Hagel, Erlangen (DE); Aleksej Hoschenko, Fürth (DE); Peter Simon Lechner, Oberasbach (DE)

(73) Assignee: RUAG AMMOTEC GMBH, Fuerth (DE)

( * ) Notice: Subject to any disclaimer, the term of this patent is extended or adjusted under 35 U.S.C. 154(b) by 680 days.

(21) Appl. No.: 12/158,356

(22) PCT Filed: Dec. 18, 2006

(86) PCT No.: PCT/EP2006/069849
§ 371 (c)(1),
(2), (4) Date: Jun. 20, 2008

(87) PCT Pub. No.: WO2007/071650
PCT Pub. Date: Jun. 28, 2007

(65) Prior Publication Data
US 2008/0308201 A1 Dec. 18, 2008

(30) Foreign Application Priority Data
Dec. 20, 2005 (DE) .................. 10 2005 061 323

(51) Int. Cl.
*C06B 41/02* (2006.01)
*C07C 205/24* (2006.01)
*C06C 7/00* (2006.01)
*C06B 41/00* (2006.01)

(52) U.S. Cl.
CPC .............. *C06C 7/00* (2013.01); *C06B 41/00* (2013.01); *C07C 205/24* (2013.01)

(58) Field of Classification Search
CPC ........ C07C 205/24; C06B 41/02; C06B 41/00
See application file for complete search history.

(56) References Cited

U.S. PATENT DOCUMENTS

| 2,352,964 | A | * | 7/1944 | McNutt et al. .................. 556/13 |
| 2,969,638 | A | * | 1/1961 | Sammons ........................ 60/219 |
| 3,238,076 | A |   | 3/1966 | Taylor et al. |
| 3,423,259 | A | * | 1/1969 | Staba .............................. 149/24 |
| 3,522,320 | A |   | 7/1970 | Bluhm et al. |
| 5,602,360 | A | * | 2/1997 | Sakamoto et al. ............ 102/220 |
| 6,165,294 | A | * | 12/2000 | Fogelzang et al. .............. 149/23 |
| 2004/0025992 | A1 | * | 2/2004 | Galluzzi ........................ 149/47 |
| 2004/0140027 | A1 | * | 7/2004 | Hagel et al. ............... 149/108.6 |
| 2005/0081969 | A1 | * | 4/2005 | Mei et al. ........................ 149/41 |
| 2005/0224147 | A1 | * | 10/2005 | Jung et al. ...................... 149/77 |

FOREIGN PATENT DOCUMENTS

| DE | 373 633 | 10/1921 |
| DE | 199 12 622 | 3/1999 |
| EP | 0 655 602 A1 | 5/1995 |
| EP | 0 658 739 A2 | 6/1995 |
| EP | 0 745 574 B1 | 9/1998 |
| GB | 1 605 333 | 2/1975 |
| JP | 07-089403 | 4/1995 |
| JP | 08-338699 | 12/1996 |
| WO | WO 97/40301 | 10/1997 |

OTHER PUBLICATIONS

Picric Acid Salts, Chemistry and Technology of Explosives, XP002447578, pp. 525-528.
Chemistry and Technology of Explosives, XP002447579, p. 220.
Lokre et al., "Electrostatic Charge Measurements on Initiators and Explosive Powders", Propellants, Explosives, Pyrotechnics, XP002447505, 1983, pp. 146-148.
Other, Nitro Derivatives of Phenols, p. 539.
Svetlov et al., Effect of Pressure on Combustion of Some Salts of Explosive Acids, XP 002447530, Trudy Kazanskogo Khimiko-Technologicheskogo Institute 1967, No. 53.
Zheng et al., Synthesis, X-ray Crystal Structure and Thermal Decomposition Mechanism of RbHTNR.infin., State Key Laboratory of Explosion Science and Technology, Beijing Institute of Technology, XP002447531.
Zheng et al., Synthesis, Crystal Structure and Thermal Behavior of Cs2 TNR.bul.2(H20)., State Key Laboratory of Explosion Science and Technology, Beijing Institute of Technology, XP002447532.
Zapar, Initiation of Explosive Powders by a Laser Beam, Department of Applied Physics and Electronics, XP008082753, Jan. 1987, pp. 18-22.
Melanie Pierce Butler, Styphnates: A Structural Investigation, Proceedings of the Eleventh Symposium on Explosives and Pyrotechnics, Franklin Research Center, Sep. 15-17, 1981.

* cited by examiner

*Primary Examiner* — Aileen B Felton
(74) *Attorney, Agent, or Firm* — Fitch, Even, Tabin and Flannery LLP

(57) ABSTRACT

The invention relates to a primer composition, to a method for producing the same and to the use of said primer composition.

28 Claims, No Drawings

PRIMER COMPOSITION

The invention provides a primer or ignition composition, a process for the production thereof and the use of the primer composition.

Conventional primer compositions, which are used, for example, in motor vehicle safety systems, have the disadvantage that they cannot be used in the engine compartment of passenger vehicles because of the low decomposition temperatures of their primer substances. Temperatures of 140° C. and above are reached in the engine compartment of a passenger vehicle, which requires a decomposition temperature of a primer substance of over 300° C. Potassium dinitrobenzofuroxanate, for example, has a decomposition temperature of about 220° C. and is therefore not suitable as a primer substance for this purpose.

An object of the present invention was to provide an primer composition which overcomes the disadvantages of the prior art. The primer composition is to comprise a primer substance that has a decomposition temperature above 300° C. Further objects of the invention were to provide a primer composition whose primer substance is free of heavy metals, whose primer substance is suitable for both mechanical and electrical primer systems, which can be used, for example, in motor vehicle safety systems, ammunition and propellant cartridges for bolt-firing tools and/or whose production is possible by simple industrial processes.

Surprisingly, it has been found that these objects are achieved by an ammunition composition comprising one or more alkali and/or alkaline-earth salts of styphnic acid (2,4,6-trinitro-1,3-dihydroxybenzene) as a primer substance, by the process for the production of this primer composition and by the use thereof according to the invention. These salts—referred to hereinbelow as styphnates for short—can be used according to the invention as a primer substance in the primer composition both individually and in admixture with one another and/or optionally in admixture with additives conventional for primer compositions, such as, for example, oxidising agents, reducing agents, sensitisers, binders, high-energy additives, combustion moderators and/or processing aids.

Preference is given according to the invention to potassium styphnate, calcium styphnate and the mixed salt thereof, potassium-calcium styphnate. Particular preference is given according to the invention to basic calcium styphnate and basic potassium-calcium styphnate.

According to the invention there can be used as additives:
1. Oxidising agents (individually or in mixtures):
   nitrates of the alkali or alkaline-earth metals or of ammonium, such as sodium nitrate or potassium nitrate, perchlorates of the alkali or alkaline-earth metals or of ammonium, peroxides of the alkaline-earth metals or of zinc, preferably zinc peroxide.
2. Reducing agents (individually or in mixtures):
   aluminium, titanium, titanium hydride, boron, boron hydride, zirconium, zirconium hydride, silicon, graphite, active carbon, carbon black, preferably titanium.
3. Sensitisers (individually or in mixtures):
   tetrazene, potassium dinitrobenzofuroxanate, diazodinitrophenol.
4. Binders (individually or in mixtures):
   adhesin, cellulose and derivatives thereof, polyvinylbutyrals, polynitropolyphenylene, polynitrophenyl ether, plexigum, polyvinyl acetate and copolymers, preferably adhesin.
6. High-energy additives (individually or in mixtures):
   hexogene, octogene, nitropenta and nitrocellulose.
7. Combustion moderators and processing aids (individually or in mixtures):
   nitrocellulose spherical powders, acetonyl acetates, salicylates, silicates, silica gels, boron nitride, preferably nitrocellulose spherical powders.

The primer composition according to the invention is distinguished by the fact that it is free of heavy metals, has high thermal stability and, when calcium styphnate and potassium-calcium styphnate are used as primer substance, by its calcium content, which by formation of calcium carbonate in the combustion residues is advantageous for weapons systems owing to the advantageous tribological properties of calcium carbonate. The decomposition temperature of the primer composition according to the invention is above 300° C. The primer composition according to the invention can be ignited both mechanically and electrically.

The production and processing of the primer composition according to the invention are carried out according to conventional processes known per se. To this end, the individual constituents of the primer composition are mixed together in a suitable manner in the required amounts.

In detail, the invention provides:
- a primer composition comprising one or more alkali and/or alkaline-earth salts of styphnic acid and/or one or more mixed salts of alkali and/or alkaline-earth salts of styphnic acid, preferably sodium styphnate, potassium styphnate, magnesium styphnate, calcium styphnate and/or potassium-calcium styphnate, particularly preferably basic calcium styphnate and/or basic potassium-calcium styphnate;
- a primer composition comprising one or more alkali and/or alkaline-earth salts of styphnic acid and/or one or more mixed salts of alkali and/or alkaline-earth salts of styphnic acid, wherein the alkali salts are the sodium and/or potassium salts of styphnic acid, preferably potassium styphnate;
- a primer composition comprising one or more alkali and/or alkaline-earth salts of styphnic acid and/or one or more mixed salts of alkali and/or alkaline-earth salts of styphnic acid, wherein the alkaline-earth salts are the magnesium and/or calcium salts of styphnic acid, preferably calcium styphnate, particularly preferably basic calcium styphnate;
- a primer composition comprising one or more alkali and/or alkaline-earth salts of styphnic acid and/or one or more mixed salts of alkali and/or alkaline-earth salts of styphnic acid, wherein the mixed salt of the alkali and/or alkaline-earth salts of styphnic acid is potassium-calcium styphnate, preferably basic potassium-calcium styphnate;
- a primer composition which, as well as comprising one or more alkali and/or alkaline-earth salts of styphnic acid and/or one or more mixed salts of alkali and/or alkaline-earth salts of styphnic acid, comprises one or more additives selected from: oxidising agents, reducing agents, sensitisers, binders, high-energy additives, combustion moderators and/or processing aids or mixtures of at least two of these additives;
- a primer composition which, as well as comprising one or more alkali and/or alkaline-earth salts of styphnic acid and/or one or more mixed salts of alkali and/or alkaline-earth salts of styphnic acid, comprises one or more additives, wherein the oxidising agent is one or more of the following substances: nitrates of the alkali or alkaline-earth metals or of ammonium, such as sodium nitrate or potassium nitrate, perchlorates of the alkali or alkaline-earth metals or of ammonium, peroxides of the alkaline-earth metals or of zinc, preferably zinc peroxide;

a primer composition which, as well as comprising one or more alkali and/or alkaline-earth salts of styphnic acid and/or one or more mixed salts of alkali and/or alkaline-earth salts of styphnic acid, comprises one or more additives, wherein the reducing agent is one or more of the following substances: aluminium, titanium, titanium hydride, boron, boron hydride, zirconium, zirconium hydride, silicon, graphite, active carbon, carbon black, preferably titanium;

a primer composition which, as well as comprising one or more alkali and/or alkaline-earth salts of styphnic acid and/or one or more mixed salts of alkali and/or alkaline-earth salts of styphnic acid, comprises one or more additives, wherein the sensitiser is one or more of the following substances: tetrazene, potassium dinitrobenzofuroxanate, diazodinitrophenol, preferably tetrazene;

a primer composition which, as well as comprising one or more alkali and/or alkaline-earth salts of styphnic acid and/or one or more mixed salts of alkali and/or alkaline-earth salts of styphnic acid, comprises one or more additives, wherein the binder is one or more of the following substances: adhesin, cellulose and derivatives thereof, polyvinylbutyrals, polynitropolyphenylene, polynitrophenyl ether, plexigum, polyvinyl acetate and copolymers, preferably adhesin;

a primer composition which, as well as comprising one or more alkali and/or alkaline-earth salts of styphnic acid and/or one or more mixed salts of alkali and/or alkaline-earth salts of styphnic acid, comprises one or more additives, wherein the high-energy additives are one or more of the following substances: hexogene, octogene, nitropenta and nitrocellulose;

a primer composition which, as well as comprising one or more alkali and/or alkaline-earth salts of styphnic acid and/or one or more mixed salts of alkali and/or alkaline-earth salts of styphnic acid, comprises one or more additives, wherein the combustion moderators and processing aids are one or more of the following substances: nitrocellulose spherical powders, acetonyl acetates, salicylates, silicates, silica gels, boron nitride, preferably nitrocellulose spherical powders;

a primer composition comprising from 10 to 90 wt. %, preferably from 20 to 80 wt. %, particularly preferably from 30 to 70 wt. %, of one or more alkali and/or alkaline-earth salts of styphnic acid and/or of one or more mixed salts of alkali and/or alkaline-earth salts of styphnic acid;

a primer composition comprising from 70 to 99.99 wt. %, preferably from 90 to 99.9 wt. %, particularly preferably from 90 to 99 wt. %, of one or more alkali and/or alkaline-earth salts of styphnic acid and/or of one or more mixed salts of alkali and/or alkaline-earth salts of styphnic acid;

a primer composition comprising from 90 to 99.99 wt. %, preferably from 95 to 99 wt. %, potassium-calcium styphnate, preferably basic potassium-calcium styphnate, and from 0.01 to 10 wt. %, preferably from 1 to 5 wt. %, binder, preferably adhesin;

the use of a primer composition comprising one or more alkali and/or alkaline-earth salts of styphnic acid and/or one or more mixed salts of alkali and/or alkaline-earth salts of styphnic acid in primer systems for motor vehicle safety systems, ammunition and/or propellant cartridges for bolt-firing tools;

the use of a primer composition comprising one or more alkali and/or alkaline-earth salts of styphnic acid and/or one or more mixed salts of alkali and/or alkaline-earth salts of styphnic acid in primer systems for motor vehicle safety systems, preferably for those used in the engine compartment of a passenger vehicle;

the use of a primer composition in primer systems that are ignited electrically.

The examples which follow are intended to explain the invention in detail without limiting it.

EXAMPLE 1: POTASSIUM-CALCIUM STYPHNATE

Basic potassium-calcium styphnate, prepared by precipitation from potassium styphnate solution with the stoichiometric addition of calcium nitrate, was investigated by atom absorption spectroscopy. The following proportions of potassium and calcium were found:

potassium: about 13 wt. %
calcium: about 7 wt. %

EXAMPLE 2: BASIC POTASSIUM-CALCIUM STYPHNATE

Potassium-calcium styphnate, prepared by adding alkali hydroxides to a potassium-calcium styphnate suspension, was investigated by atom absorption spectroscopy. The following proportions of potassium and calcium were found:

potassium: about 11.5 wt. %
calcium: about 12 wt. %

Table 1 shows the decomposition temperatures and the friction and impact sensitivities of the substances. The friction and impact sensitivities were measured by methods of the Bundesanstalt für Materialforschung (BAM), while the decomposition temperatures were measured by thermogravimetric analysis (Mettler) with a heating rate of 10° C. per minute.

TABLE 1

|  | Potassium-calcium styphnate | Basic potassium-calcium styphnate | Basic calcium styphnate |
|---|---|---|---|
| Friction sensitivity in N | 9 | 9 | 9 |
| Impact sensitivity in J | 3 | 3 | 4 |
| Decomposition temperature in ° C. | 345 | 340 | 335 |

These styphnates are mixed with additives conventional for primer compositions in the required relative amounts by methods known per se.

The invention claimed is:

1. A primer composition comprising:
    at least one styphnate selected from the group consisting of potassium-calcium styphnate, basic calcium styphnate and basic potassium-calcium styphnate; and
    one or more additives selected from:
        an oxidising agent selected from the group consisting of nitrates of the alkali or alkaline-earth metals or of ammonium, perchlorates of the alkali or alkaline-earth metals or of ammonium, peroxides of the alkaline-earth metals, of zinc and mixtures of these components;
        a reducing agent selected from the group consisting of aluminium, titanium, titanium hydride, boron, boron hydride, zirconium, zirconium hydride, silicon, graphite, active carbon, carbon black and mixtures of these components;
a sensitizer selected from the group consisting of tetrazene, potassium dinitrobenzofuroxanate, diazodinitrophenol and mixtures of these components;
a binder selected from the group consisting of adhesin, cellulose and derivatives thereof, polyvinylbutyrals, polynitropolyphenylene, polynitrophenyl ether, plexigum, polyvinyl acetate, copolymers and mixtures of these components;
a high-energy additive selected from the group consisting of hexogene, octogene, nitropenta and nitrocellulose and mixtures of these components; and
a combustion moderator or processing aid selected from the group consisting of nitrocellulose spherical powders, acetonyl acetates, salicylates, silicates, silica gels, boron nitride and mixtures of these components;
wherein the primer composition is configured to have a decomposition temperature above 300° C.

2. The primer composition according to claim 1, characterised in that the primer composition has a friction sensitivity of 9 N and an impact sensitivity of 3-4 J.

3. A passenger vehicle comprising an engine compartment provided with a motor vehicle safety system including the primer composition according to claim 1.

4. The primer composition according to claim 1, characterised in that it comprises an oxidising agent selected from the group consisting of nitrates of the alkali or alkaline-earth metals or of ammonium, perchlorates of the alkali or alkaline-earth metals or of ammonium, peroxides of the alkaline-earth metals, of zinc and mixtures of these components.

5. The primer composition according to claim 1, characterised in that it comprises a reducing agent selected from the group consisting of aluminium, titanium, titanium hydride, boron, boron hydride, zirconium, zirconium hydride, silicon, graphite, active carbon, carbon black and mixtures of these components.

6. The primer composition according to claim 1, characterised in that it comprises a sensitiser selected from the group consisting of tetrazene, potassium dinitrobenzofuroxanate, diazodinitrophenol and mixtures of these components.

7. The primer composition according to claim 1, characterised in that it comprises a binder selected from the group consisting of adhesin, cellulose and derivatives thereof, polyvinylbutyrals, polynitropolyphenylene, polynitrophenyl ether, plexigum, polyvinyl acetate, copolymers and mixtures of these components.

8. The primer composition according to claim 1, characterised in that it comprises high-energy additives selected from the group consisting of hexogene, octogene, nitropenta and nitrocellulose and mixtures of these components.

9. The primer composition according to claim 1, characterised in that it comprises combustion moderators and processing aids selected from the group consisting of nitrocellulose spherical powders, acetonyl acetates, salicylates, silicates, silica gels, boron nitride and mixtures of these components.

10. The primer composition according to claim 1, characterised in that it comprises from 10 to 90 wt. % of the at least one styphnate selected from the group consisting of potassium-calcium styphnate, basic calcium styphnate and basic potassium-calcium styphnate.

11. The primer composition according to claim 1, characterised in that it comprises from 70 to 99.99 wt. % of the at least one styphnate selected from the group consisting of potassium-calcium styphnate, basic calcium styphnate and basic potassium-calcium styphnate.

12. The primer composition according to claim 1, characterised in that it comprises from 90 to 99.99 wt. % basic potassium-calcium styphnate and from 0.01 to 10 wt. % binder.

13. A primer system for ammunition comprising the primer composition according to claim 1.

14. The primer composition according to claim 1, characterised in that it comprises potassium-calcium styphnate.

15. The primer composition according to claim 1, characterised in that it comprises at least one styphnate selected from the group consisting of basic calcium styphnate and/or basic potassium-calcium styphnate.

16. The primer composition according to claim 1, characterised in that it comprises from 20 to 80 wt. % of the at least one styphnate selected from the group consisting of potassium-calcium styphnate, basic calcium styphnate and basic potassium-calcium styphnate.

17. The primer composition according to claim 1, characterised in that it comprises from 30 to 70 wt. % of the at least one styphnate selected from the group consisting of potassium-calcium styphnate, basic calcium styphnate and basic potassium-calcium styphnate.

18. The primer composition according to claim 11, characterised in that it comprises 90 to 99.9 wt. % of the at least one styphnate selected from the group consisting of potassium-calcium styphnate, basic calcium styphnate and basic potassium-calcium styphnate.

19. The primer composition according to claim 11, characterised in that it comprises 90 to 99 wt. % of the at least one styphnate selected from the group consisting of potassium-calcium styphnate, basic calcium styphnate and basic potassium-calcium styphnate.

20. The primer composition according to claim 12, characterised in that it comprises from 95 to 99 wt. % basic potassium-calcium styphnate, and from 1 to 5 wt. %, binder, and in that the binder comprises adhesin.

21. A propellant cartridge for a bolt-firing tool comprising the primer composition according to claim 1.

22. A primer system for a motor vehicle safety system comprising the primer composition according to claim 1.

23. The primer system for a motor vehicle safety system according to claim 22, characterised in that the primer system is provided in an engine compartment of a passenger vehicle.

24. The primer composition according to claim 1, characterised in that it comprises basic calcium styphnate.

25. The primer composition according to claim 1, characterised in that it comprises basic potassium-calcium styphnate.

26. The primer composition according to claim 1, characterised in that the primer composition has a decomposition temperature of at least 335° C.

27. The primer composition according to claim 25, characterised in that the primer composition has a decomposition temperature of at least 335° C.

28. The primer composition according to claim 1, characterised in that it the primer composition has a friction sensitivity of 9 N and an impact sensitivity of 3-4 J.

* * * * *